(12) United States Patent
Kranz et al.

(10) Patent No.: US 6,312,456 B1
(45) Date of Patent: Nov. 6, 2001

(54) BIOCOMPATIBLE STENT WITH RADIOPAQUE MARKERS

(75) Inventors: Curt Kranz, Berlin; Heinz Mueller, Erlangen, both of (DE)

(73) Assignee: Biotronik Mass-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 08/985,756

(22) Filed: Dec. 5, 1997

(30) Foreign Application Priority Data

Dec. 10, 1996 (DE) ................................ 196 53 720

(51) Int. Cl.[7] .................................................. A61F 2/06
(52) U.S. Cl. ......................................... 623/1.13; 623/1.34
(58) Field of Search .................... 623/1, 11, 1.1–1.22; 606/195

(56) References Cited

U.S. PATENT DOCUMENTS

| | | | | |
|---|---|---|---|---|
| 4,830,003 | * | 5/1989 | Wolf et al. ........................... | 128/343 |
| 5,485,667 | | 1/1996 | Kleshinski . | |
| 5,591,197 | * | 1/1997 | Orth et al. ........................... | 606/198 |
| 5,735,896 | * | 4/1998 | Amon et al. ........................... | 623/11 |
| 5,817,152 | * | 10/1998 | Birdsall et al. ........................... | 623/1 |
| 5,824,045 | * | 10/1998 | Alt ........................................... | 623/1 |

FOREIGN PATENT DOCUMENTS

| | | |
|---|---|---|
| 0364787B1 | 4/1990 | (EP) . |
| 0679372A2 | * 2/1995 | (EP) . |
| 0709068A2 | 5/1996 | (EP) . |
| WO 95/30384 | 11/1995 | (WO) . |
| WO 92/26689 | 9/1996 | (WO) . |

* cited by examiner

*Primary Examiner*—Corrine McDermott
*Assistant Examiner*—Hieu Phan
(74) *Attorney, Agent, or Firm*—Venable, Baetjer; Robert Kinberg; Eric J. Weierstall

(57) ABSTRACT

A stent, in particular a coronary stent, includes a thin-walled, hollow-cylindrical base body of an X-ray transparent material, the surface area of which has an open-worded, net-shaped design owing to recesses. The stent has at least one X-ray opaque element or region, wherein the X-ray opaque element or the X-ray opaque region extends essentially in a linear direction over at least a portion of the circumference of the stent located at least one end region of the stent while the rest of the stent remains X-ray transparent.

8 Claims, 3 Drawing Sheets

BIOCOMPATIBLE STENT WITH RADIOPAQUE MARKERS

BACKGROUND OF THE INVENTION

The invention concerns a stent, in particular a coronary stent, as an intraluminal expansion element comprising a thin-walled, hollow-cylindrical base body of an X-ray transparent material having a surface area which has an open-worked, net shaped design owing to recesses and comprising at least one X-ray opaque element or region.

European patent document EP-B1 0 364 787 discloses an expandable, intraluminal element with at least one thin-walled, tube-shaped segment (in the following called a stent). The surface area of the stent has an open-worked, net-shaped design and comprises recesses, which are limited by web-like elements with low material strength that extend in a straight-line in the axial and circumferential directions. The web-like elements consist of the remaining tube wall where the material was removed in the region of the recesses. Four of these web-like elements, together with the connecting pieces provided at their ends, form a so-called "expansible region" of the stent surface area.

Such stents are expanded during an operation, e.g. to remove a stenosis, under the effect of forces that act from the inside toward the outside and by using a tubular dilator admitted with compressed gas. Despite the deformation, the stent retains its tubular shape and dilates the vessel that is restricted as a result of deposits.

The above-described stents are produced from biocompatible materials such as stainless steel, titanium or other metals. Titanium stents have proven to be particularly useful with respect to physical tolerance, options for medical use and mechanical workability.

However, for the wall thicknesses used for stents, the metals used most often are essentially X-ray transparent, and stents fashioned from these cannot be seen by the physician when using X-rays. Nevertheless, the identification of the stent position with the aid of a suitable monitor has proven to be very critical for the correct handling.

A stent visible in an X-ray is disclosed in European patent document EP-A-O 709 068, for which the visibility in the X-ray is achieved through a coating with a metal having a high atomic weight or through expanded, e.g. ring-shaped, extensions on the individual ends of the meshes.

German patent document DE-U-296 07 916 discloses a stent with a segment visible in the X-ray, which is produced in particular by welding together two prefabricated hollow cylinders made of X-ray transparent or X-ray reflecting material.

The accuracy of the stent position determination can still be improved for both of the aforementioned arrangements.

SUMMARY OF THE INVENTION

It is therefore an object of the invention to specify a stent of the aforementioned generic type, for which the position inside the body of a patient can be determined very precisely with the aid of X-rays.

The above and other objects are accomplished in accordance with the invention by the provision of a stent comprising a thin-walled, hollow-cylindrical base body of an X-ray transparent material having a surface area which has an open-worked, net shaped design owing to recesses and comprising at least one X-ray opaque element or region which extends essentially in a linear direction over at least a portion of the stent circumference located at least one end region of the stent while the rest of the stent remains X-ray transparent.

The invention includes the technical teaching that for the identification with X-rays of a stent, a sufficient contrast can be achieved and simultaneously a very precise determination of the angular position of the stent inside the body is possible, even if only a very limited region or a single element, which is essential to the determination of the angular position, is designed to be visible in the X-ray. In particular, this is a linear region adapted to the circumferential outline of the stent and even more specifically a ring or ring-shaped segment, for which the projection in the X-ray picture provides exact information not only concerning the location, but also the orientation of the stent.

The end regions of the stent in particular are suitable for providing this region or element. If the stent length is known, the exact stent position can be determined even with a single, X-ray opaque element.

It is important that the X-ray opaque modification does not essentially impair the expansion capability of the stent.

The X-ray opaque or reflecting element or the corresponding region is designed to have an "expansion reserve" for this. It is also possible to provide a coating for a regularly deformable, X-ray transparent stent segment, which reflects the X-rays. This coating preferably is applied with a vapor-deposit or vacuum-HF-coating method (sputtering etc). X-ray optical identifiers of almost any shape can be generated in this way, so that the physician can securely control position, direction and form of the stent. In accordance with a different embodiment, the curved, rounded connecting pieces for the web-like elements at the end of the stent are themselves composed of X-ray opaque material.

Gold, silver or tantalum in particular are provided as material for the X-ray opaque element for the above-described embodiments of the stent according to the invention, which is preferably produced from titanium, since these metals have the required biocompatibility in the X-ray range, in addition to a relatively high reflection factor.

The use of laser technology is provided for the necessary soldering connections and removal operations in the stent production and for the hollow-cylindrical tube rounds, required for the stent production, necessitated in particular by the small dimensions of the parts.

In order to design the linear or the rounded segments (in the not-expanded state) to be X-ray opaque at the ends or in the center of the stent, a meandering, curved thread (e.g. of Ta) of a X-ray opaque material is welded onto or welded into a thin-wall stent hollow cylinder (for example of Ti) The material pairing Ti-Ta is particularly favorable because these metals are soluble into each other and can therefore be easily welded together.

This embodiment of the stent according to the invention is very compatible with the body and exhibits excellent deformability. An outer micro-coating of amorphous silicon carbide additionally counteracts a thrombosis formation.

Owing to the fact that during the expansion of the axially extending web-like elements due to deformation, the stent can adapt only to a limited at the stent end to the shape of the tissue for a blood vessel to be expanded in this area, where the effectiveness of the stent ends, the material cross section of the web-like elements of the stent is reduced at the stent end in accordance with one advantageous modification In a favorable manner, this ensures that a "flowing" transition with variable, compensating change in the cross section occurs, if possible, from a vessel area expanded by the stent to the adjoining vessel area that is free of a stenosis.

This reduction in the cross section is preferably created while maintaining the radial dimensions in tangential direction, so that the stent can be produced from tube rounds by means of a laser cutting tool and by cutting out the recessed regions. With the rigidity of the stents reduced in this way toward the end region, it is particularly important that this reduced rigidity is not increased again by adapting the design of the X-ray opaque regions or elements.

BRIEF DESCRIPTION OF THE DRAWINGS

Further advantageous modifications of the invention are shown in more detail with the aid of the figures, together with the description of the preferred embodiment of the invention. Shown are:

FIG. 2 another embodiment of the invention in a view from the side, as well as

DETAILED DESCRIPTION OF THE DRAWINGS

Figure 1:
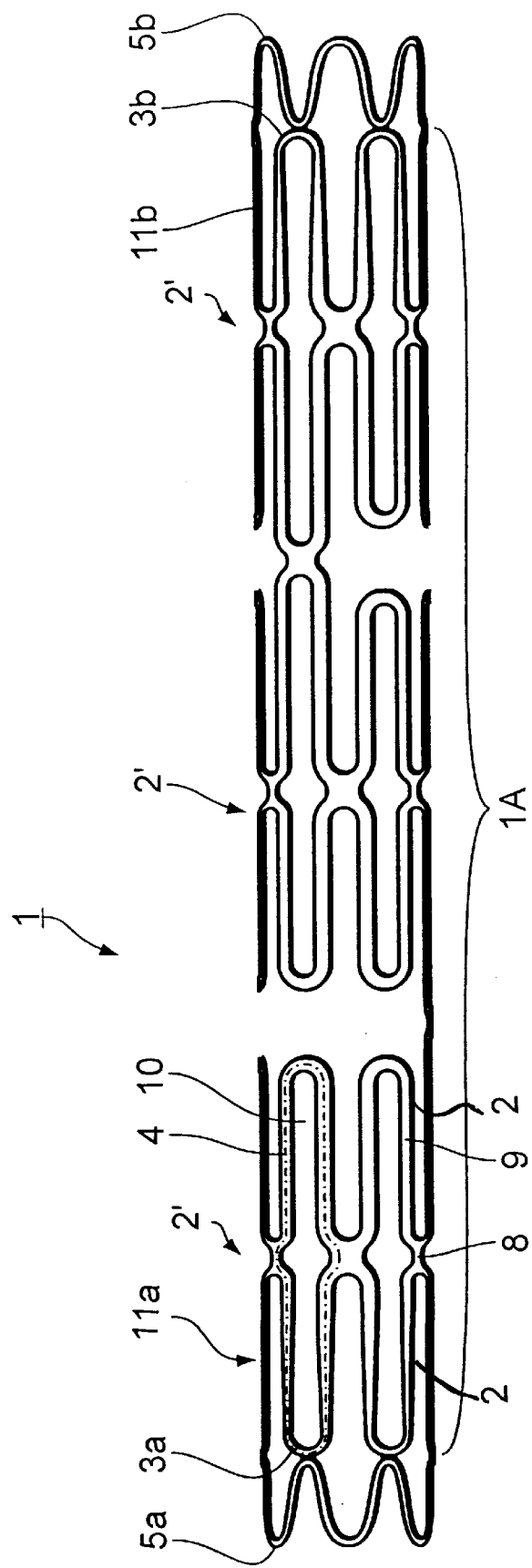
FIG. 1 an embodiment of the invention in a view from the side.

FIG. 1 shows a stent 1 comprised of a hollow-cylindrical base body 1A made of titanium, with a plurality of recesses 10, which are respectively enclosed by expansible meshes in the form of buckled rings. These are referred to in the following as "expansible regions" and are marked in one example with a dash-dot line 4. These expansible regions 4 are formed by circumferential, narrow, web-like elements 9 with a rectangular cross section and are distinguished in that they enclose a recess 10, essentially in a ring-shaped design.

In the completely expanded state (not shown in the drawing), the expansible regions 4 have a nearly polygonal shape. They are shaped (primarily) during the production in such a way that following the inserting of the stent 1 into a vessel through dilating with a balloon catheter, they change with minimal deformation to the polygonal shape.

The stent 1 shown in FIG. 1 is divided into several segments 2 which are lined up in axial direction and have a structurally identical design. Identically designed coupling elements 8 are provided to connect the expansible regions 4 of the individual stent segments 2, as well as the neighboring segments 2'. The material cross section of the meshes and thus also the rigidity are continuously reduced on both ends of the hollow cylinder 1A.

On its two ends 11a and 11b, the hollow cylinder 1A respectively comprises one welded-on thread 5a or 5b, configured in a meandering shape and made of a tantalum alloy. The X-ray opaque threads 5a, 5b are respectively connected through individual laser soldering points to the frontal mesh curves 3a and 3b for the Ti hollow cylinder. During the stent dilatation, the threads 5a, 5b expand to a stretched, ring-shaped state. In order to adapt to the hollow cylinder ends, the material cross section and alloy composition of the Ta threads are selected such that they follow the characteristic curve for the rigidity in the stent end regions. The weakening of the stent end regions is therefore also not affected by the X-ray opaque elements.

Figure 2:
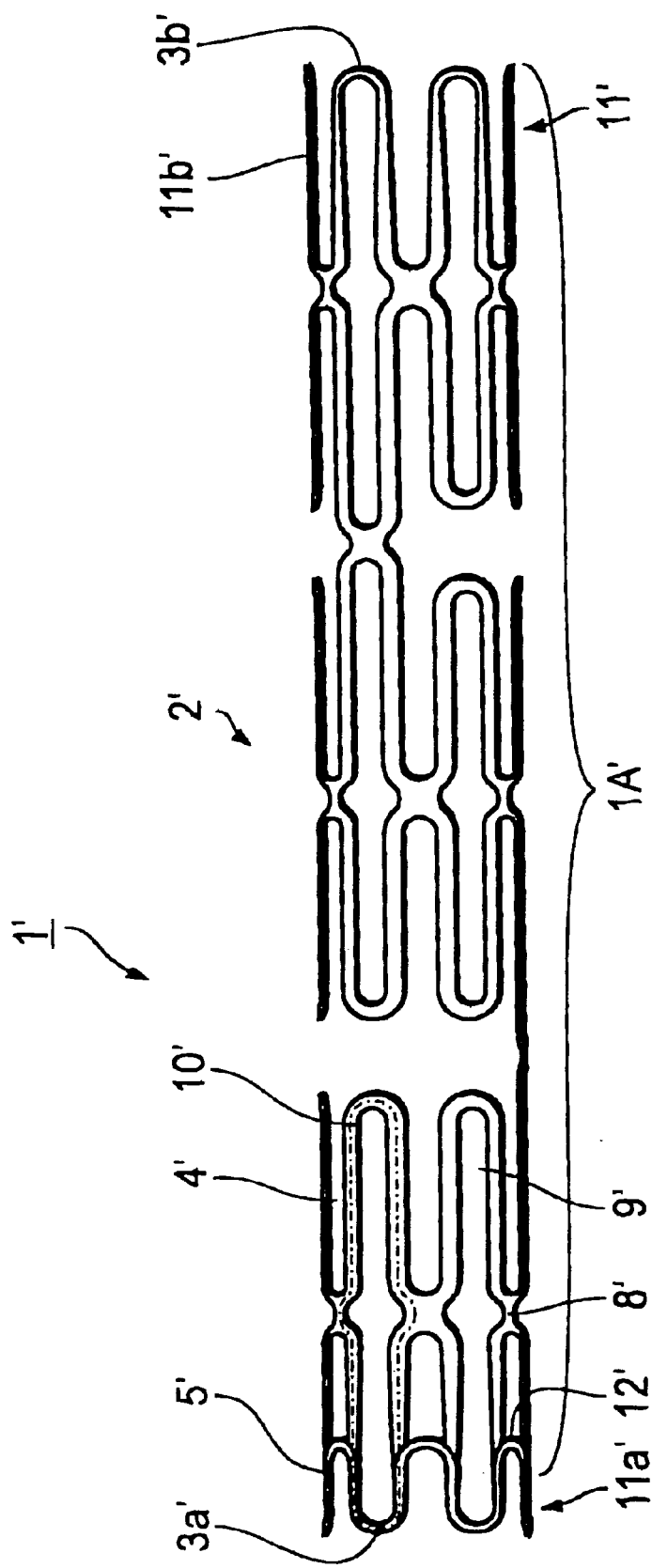
Figure 3:
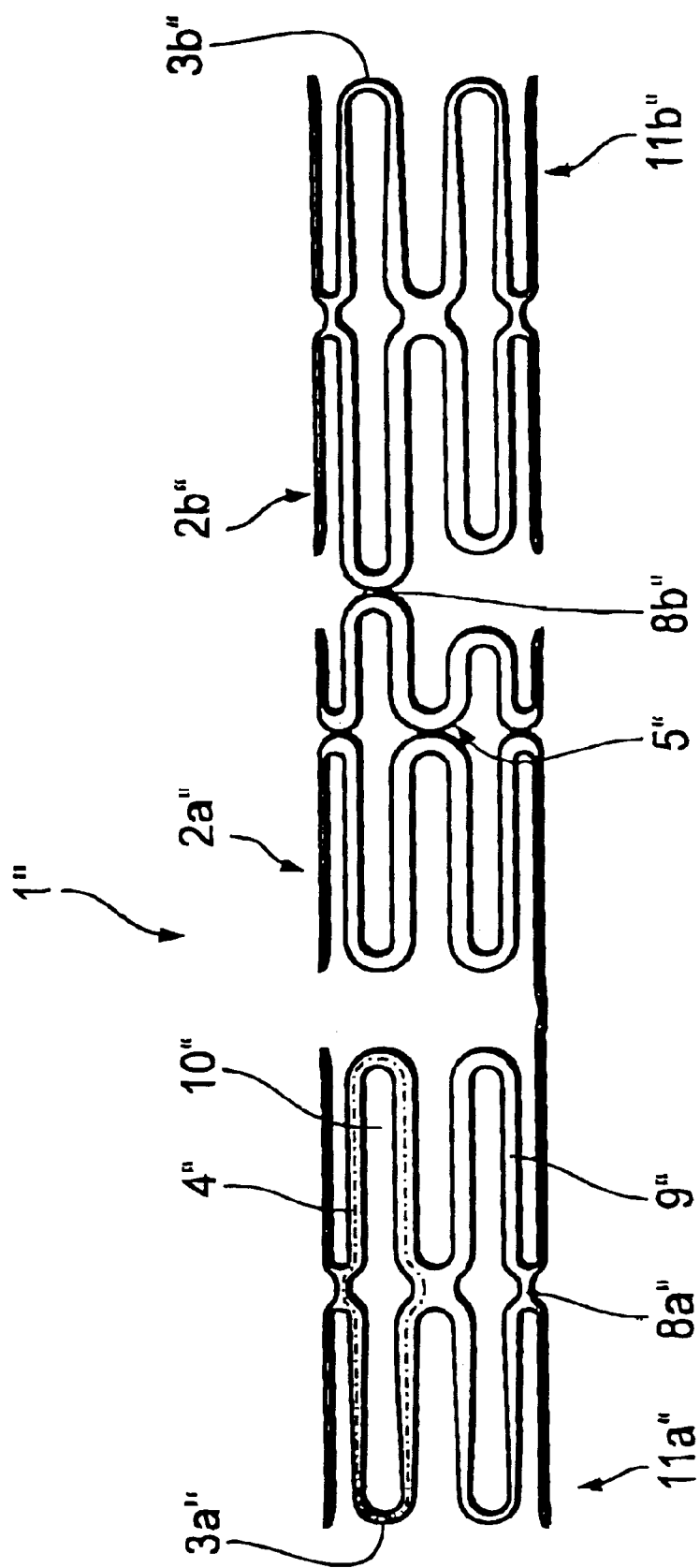
FIG. 3 a favorable modification of the exemplary embodiment of the invention shown in FIG. 2, in a view from the side.

The stents 1' and 1", shown as a side view in FIGS. 2 and 3, have elements or regions that are coated with X-ray opaque materials or are composed in part of such materials. Since this hardly changes the outside contour, the flow qualities of the stent are also not fundamentally influenced. Elements resembling those in FIG. 1 are given the same reference numbers.

In accordance with FIG. 2, the curved segments 3a' and 3b' of the expansible regions 4' at the one end 11a' of the stent 1' are composed in part of X-ray opaque material and, with the aid of additional, bent webs 12' that are composed completely of an X-ray opaque material, are connected to each other to form a closed marker thread. This configuration can be formed by welding a thread 5' of X-ray opaque material in a meandering design onto the curved segments, which are pre-fabricated to be correspondingly weak. Gold, silver or another material with low X-ray permeability are suitable for the coating. The other end 11b' of the stent 1' in this case is not provided with an X-ray identifier.

The exemplary embodiment according to FIG. 3 shows that an X-ray opaque thread 5" is inserted into the center region of stent 1". In the region of the tangentially extending webs, this thread is welded to the neighboring X-ray transparent segments 2a" and 2b", so that on the whole, the stent 1" comprises compound webs 8b" in addition to the webs 8a" composed of a homogeneous material.

The above-mentioned X-ray opaque or reflecting elements or regions should be at least 15 μm wide and preferably 75 μm wide for a completely accurate identification in the X-ray picture, wherein the condition must be met that it extends essentially in linear direction. The element is preferably attached to the outside surface area of the base body to ensure good flow qualities of the stent as well as for production technology reasons.

In order to avoid stenoses or to reduce the danger of a stenosis, the stent has an outer coating of amorphous silicon carbide, which also covers the X-ray opaque elements or regions, so that a uniform outer surface structure exists.

The embodiment of the invention is not limited to the aforementioned, preferred exemplary embodiments. Rather, a number of variants are useful, which make use of the solution shown, even if the embodiment is different.

Thus, it is possible to have embodiments where the X-ray opaque element does not extend over the complete circumference of the stent. Modifications of the production method are also possible and in particular, it is possible on principle to have a coating of the X-ray transparent regions of the stent with the X-ray opaque material in place of a welding.

What is claimed is:

1. A stent comprising a thin-walled, hollow-cylindrical base body of an X-ray transparent material, having a surface area which has an open-worked, net shaped design owing to recesses, and comprising at least one X-ray opaque element or region which extends essentially in a linear direction over at least a portion of the stent circumference located at at least one end region of the stent while the rest of the stent remains X-ray transparent, wherein the at least one end region comprises curved segments of the surface area of the stent and the segments are themselves composed of an X-ray opaque material.

2. A stent according to claim 1, wherein the X-ray opaque element or the X-ray opaque region extends in the shape of a meandering thread essentially around the complete circumference of the stent.

3. A stent according to claim 1, wherein the X-ray opaque element or the X-ray opaque region is provided on at least one of the end regions and attached on an outside surface of the base body.

4. A stent according to claim 1, wherein the X-ray opaque element is attached to the X-ray transparent base body through laser point-welding.

5. A stent according to claim 1, wherein the X-ray opaque element or the X-ray opaque region is composed from any one of stainless steel, gold, silver, tantalum, and an alloy containing at least one of these metals.

6. A stent according to claim 1, wherein the X-ray transparent base body is essentially composed of titanium and the X-ray opaque element or the X-ray opaque region is essentially composed of tantalum.

7. A stent according to claim 1, including an amorphous silicon carbide coating on an outside surface of the stent which includes the X-ray opaque element or the X-ray opaque region.

8. A stent according to claim 1, wherein the at least one end region comprises curved segments of the surface area of the stent and the segments are themselves composed of an X-ray opaque material.

* * * * *